United States Patent [19]

Coy et al.

[11] Patent Number: 5,569,741
[45] Date of Patent: Oct. 29, 1996

[54] CYCLIC OCTAPEPTIDE NEUROMEDIN B RECEPTOR ANTAGONISTS

[75] Inventors: David H. Coy, New Orleans, La.; John E. Taylor, Upton, Mass.

[73] Assignees: Biomeasure, Inc., Milfor, Mass.; The Administrators of the Tulane Educational Fund, New Orleans, La.

[21] Appl. No.: 352,392

[22] Filed: Dec. 8, 1994

Related U.S. Application Data

[63] Continuation-in-part of Ser. No. 78,419, Jun. 17, 1993, Pat. No. 5,462,926, which is a continuation-in-part of Ser. No. 919,537, Jul. 27, 1992, abandoned.

[51] Int. Cl.$^6$ .............................. A61K 38/00; C07K 5/00; C07K 7/00; C07K 17/00
[52] U.S. Cl. ........................... 530/311; 530/317; 530/328
[58] Field of Search .................................. 530/311, 328, 530/317; 514/15, 16, 17

[56] References Cited

U.S. PATENT DOCUMENTS 5,003,011  3/1991  Coy et al. ............................... 530/328

FOREIGN PATENT DOCUMENTS

| 0215171 | 2/1985 | European Pat. Off. . |
| 0389180 | 3/1987 | European Pat. Off. ......... C07K 7/06 |
| 89/04666 | 11/1987 | European Pat. Off. . |
| 0298732 | 7/1988 | European Pat. Off. . |
| 0395417 | 2/1990 | European Pat. Off. . |
| 91/09056 | 12/1990 | European Pat. Off. . |
| 0417454 | 3/1991 | European Pat. Off. . |

OTHER PUBLICATIONS

Smith et al., "Principles of Biochemistry: General Aspects", Seventh Edition, published 1983 by MacGraw-Hill (N.Y.), pp. 32–33 and 617, see entire document.
PCT search report dated 1 Apr. 1996.
Benya et al., "Neuromedin B Receptors Retain Functional Expression when Transfected into BALB 3T3 Fibroblasts: Analysis of Binding, Kinetics, Stoichiometry, . . . ", Molecular Pharmacology, 42:1058–1068, 1992.
Coy et al., "Solid Phase Reductive Alkylation Techniques in Analogue Peptide Bond and Side–Chain Modification", Tetrahedron, 44:835–841, 1988.
Kawai et al., "Effects of Neuromedin B and GRP–10 on Gastrin and Insulin Release from Cultured Tumor Cells of a Malignant Gastrinoma", Endocrinol. Japan. 37 (6), 857–865, 1990.
Ladenheim et al., "Capsaicin Attenuates bombesin–induced Suppression of Food Intake", Am. J. Physiol. 260 (Regulatory Integrative Comp. Physiol. 29): R263–R266, 1991.
Moody et al., "Neuromedin B Binds with High Affinity, Elevates Cytosolic Calcium and Stimulates the Growth of Small–Cell Lung Cancer Cell Lines", The Journal of Pharmacology & Experi. Therapeutics, 263:311–317, 1992.
Orbuch et al., "Discovery of a Novel Class of Neuromedin B Receptor Antagonists, Substituted Somatostatin Analogues", Molecular Pharmacology, 44:841–850, 1993.

Sasaki et al., "Solid–Phase Synthesis and Biological Properties of ψ[CH$_2$NH] Pseudopeptide Analogues of a Highly Potent Somatostatin Octapeptide", J. Med. Chem. 30:1162–1166, 1987.
Wada et al., "cDNA Cloning, Characterization, and Brain Region–Specific Expression of a Neuromedin–B–Preferring Bombesin Receptor", Neuron, 6:421–430, 1991.
Wang et al., "Activation of Neuromedin B–Preferring Bombesin Receptors on Rat Glioblastoma C–6 Cells Increases Cellular CA$^{2+}$ and Phosphoinositides", Biochem. J. 286:641–648, 1992.
STN international "Fast Notes" paper.

Primary Examiner—Avis M. Davenport
Attorney, Agent, or Firm—Fish & Richardson P.C.; William E. McGowan

[57] ABSTRACT

A cyclic octapeptide of the formula:

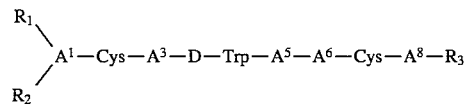

wherein:

$A^1$ is D-Nal or D-Trp;

$A^3$ is Phe, F$_5$-Phe, or X-Phe wherein X is a halogen, NO$_2$, CH$_3$, or OH;

$A^5$ is —NH—CH(Y)—CO— wherein Y is (CH$_2$)$_m$—R$_4$—N(R$_5$)(R$_6$) or (CH$_2$)$_n$—R$_4$—NH—C(R$_7$)—N(R$_5$) (R$_6$);

$A^6$ is the D— or L— isomer of Thr, Leu, Ile, Nle, Val, and Abu;

$A^8$ is Nal or Trp;

m is 1, 2, or 3;

n is 1, 2, 3, 4 or 5;

each of $R_1$ and $R_2$, independently, is H, E, COE, or COOE wherein E is C$_{1-12}$ alkyl, C$_{2-12}$ alkenyl, C$_{2-12}$ alkynyl, phenyl, naphthyl, C$_{7-12}$ phenylalkyl or alkylphenyl, C$_{8-12}$ phenylalkenyl or alkenylphenyl, C$_{8-12}$ phenylalkynyl or alkynylphenyl, C$_{11-20}$ naphthylalkyl or alkylnaphthyl, C$_{12-20}$ naphthylalkenyl or alkenylnaphthyl, or C$_{12-20}$ naphthylalkynyl or alkynylnaphthyl, provided that when one of $R_1$ or $R_2$ is COE or COOE, the other must be H;

$R_4$ is C$_6$H$_4$ or absent;

$R_7$ is =NR$_8$, =S, or =O; and each of $R_3$, $R_5$, $R_6$, and $R_8$, independently, is H or E.

24 Claims, 1 Drawing Sheet

CYCLIC OCTAPEPTIDE NEUROMEDIN B RECEPTOR ANTAGONISTS

STATEMENT AS TO FEDERALLY SPONSORED RESEARCH

This invention was made with support from the National Institutes of Health (Grant No. CA 45153). Accordingly, the U.S. government may have certain rights in the invention.

CROSS REFERENCE TO RELATED APPLICATIONS

This application is a continuation-in-part of U.S. patent application Ser. No. 08/078,419, filed Jun. 17, 1993, now U.S. Pat. No. 5,462,926, which is a continuation-in-part of U.S. patent application Ser. No. 07/919,537, filed Jul. 27, 1992, abandoned.

BACKGROUND OF THE INVENTION

The mammalian bombesin (Bn)-related peptides, gastrin-releasing peptide (GRP), neuromedin B (NMB), and neuromedin C (NMC) have a wide range of biological effects. These include chemotaxis, contraction of smooth muscle stimulation, and the release of numerous gastrointestinal hormones. GRP and NMB are also active in the central nervous system, affecting thermoregulation, behavioral effects, satiety, maintenance of circadian rhythm, and inhibition of TSH release. Bn-related peptides function as a growth factor in numerous normal cells (e.g., stomal, epithelial, and neuroendocrine cells) as well as neoplastic cells such as human small cell lung cancer cells, non-small cell lung cancer cells, rat hepatocellular tumor cells, prostatic cells and breast adenocarcinoma cells.

Recent structure and cloning studies demonstrate that Bn-related peptides mediate the actions of two distinct receptor classes. GRP has a high affinity, and NMB has a low affinity, for the GRP-preferring class or subtype (GRP receptor or GRP-R). In contrast, GRP has a low affinity, and NMB has a high affinity, for the other class, the NMB-preferring subtype (NMB receptor or NMB-R). Both receptor classes are present throughout the central nervous system and the gastrointestinal tract.

Native somatostatin, somatostatin-14 (SS-14), has been shown to inhibit the cross-linking of $^{125}$I-GRP to a 120 kD protein in Triton® extracts of 3T3 cells and human small cell lung cancer cells which are known to possess bombesin receptors. Recently, somatostatin octapeptide analogs have also demonstrated binding affinity to NMB-R in Orbuch, et al., *Mol. Pharmacol.*, 44:841 (1993). These analogs, however, also maintain a substantial activity for somatostatin receptors.

SUMMARY OF THE INVENTION

Abbreviations
Nal =3-(2-naphthyl)-alanine or 3-(1-naphthyl)-alanine
Bpa =3-(4-biphenyl)-alanine
X-Phe =phenylalanine with a p-, o- or m-substituent, such as —OH, $CH_3$, $NO_2$, and halogen, on the phenyl ring, e.g., 3-(4-chloropheny, l)-alanine
$F_5$Phe =3-(pentafluorophenyl)-alanine
Nle =norleucine
Me-Trp =Trp with a methyl-substituted indolyl nitrogen
Dab =2,4-diamino butyric acid
Abu =2-amino butyric acid The present invention relates to cyclic octapeptides which have both high affinity and high selectivity for the NMB receptor and are encompassed by the following formula (I):

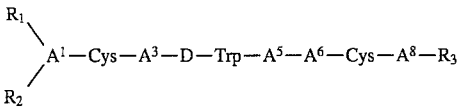

$A^1$ is the D-isomer of Nal or Trp, and is preferably D-Nal. $A^3$ is $F_5$-Phe or ortho-, para-, or meta-substituted X-Phe wherein X is halogen, $NO_2$, $CH_3$ or OH. $A^3$ is preferably Phe or para-substituted X-Phe, where X is Cl, F, or OH. $A^5$ is —NH—CH(Y)—CO— wherein Y is $(CH_2)_m$—$R_4$—$N(R_5)(R_6)$ or $(CH_2)_n$—$R_4$— NH—$C(R_7)$—$N(R_5)$ $(R_6)$. In one aspect, $A^5$ is —NH—CH(Y)—CO— where Y is $(CH_2)_m$—$R_4$—$N(R_5)(R_6)$, and preferably Orn, Dab, 7-amino-phenylalanine, and 2,3-diamino propionic acid. In another aspect, $A^5$ is —NH—CH(Y)—CO— where Y is $(CH_2)_n$—$R_4$—NH— $C(R_7)$—$N(R_5)(R_6)$, and is preferably Arg or 7-guandindylphenylalanine. $A^6$ is the D— or L— isomer of Thr, Leu, Ile, Nle, , Val, Nal, Trp, Me-Trp, Abu, Bpa, Phe, $F_5$-Phe, or X-Phe wherein X is a halogen, $NO_2$, $CH_3$, or OH. $A^6$ is preferably the D— or L— isomer of Thr, Leu, Ile, Nle, Trp, Val, and Abu. $A^8$ is Nal or Trp, and is preferably Nal. Subscript m is 1, 2, or 3, and preferably 2 or 3; n is 1, 2, 3, 4 or 5, and preferably 2, 3, or 4. Each of $R_1$ and $R_2$, independently, is H, E, COE, or COOE. E is a hydrocarbon of between 1 and 25 carbon atoms; substituted or unsubstituted; saturated or unsaturated; straight chain or branched; cyclic, acyclic, or polycyclic. Examples of E include $C_{1-12}$ alkyl, $C_{2-12}$ alkenyl, $C_{2-12}$ alkynyl, phenyl, naphthyl, $C_{7-12}$ phenylalkyl or alkylphenyl, $C_{8-12}$ phenylalkenyl or alkenylphenyl, $C_{8-12}$ phenylalkynyl or alkynylphenyl, $C_{11-20}$ naphthylalkyl or alkylnaphthyl, $C_{12-20}$ naphthylalkenyl or alkenylnaphthyl, or $C_{12-20}$ naphthylalkynyl or naphthylalkynyl, provided that when one of $R_1$ or $R_2$ is COE or COOE, the other must be H. $R_3$, $R_5$, $R_6$, $R_8$ are each independently H or E. Each of $R_3$, $R_5$, $R_6$, and $R_8$ is preferably H or a $C_{1-10}$ hydrocarbon, such as alkyl, alkenyl, alkylphenyl, phenyl, and phenylalkyl, including $C_{1-5}$ alkyl. Each of $R_5$ and $R_6$ is more preferably H. $R_4$ is $C_6H_4$ or absent, and preferably is absent. $R_7$ is =$NR_8$, =S, or =O, and preferably =$NR_8$, and more preferably $R_7$ is =NH. Preferred octapeptides encompassed by the above formula (I) of the invention include $H_2$-D-Nal-Cys-Tyr-D-Trp-Arg-Val-Cys-Nal-$NH_2$ (peptide Arg$^5$); $H_2$-D-Nal-Cys-Tyr-D-Trp-Dab-Val-Cys-Nal-$NH_2$ (peptide Dab$^5$); and $H_2$-D-Nal-Cys-Tyr-D-Trp-Orn-Val-Cys-Nal-$NH_2$ (peptide Orn$^5$).

In formula (I), the N-terminus is at the left and the C-terminus at the right in accordance with the conventional representation of a polypeptide chain. The symbol $A^1$, $A^2$, or the like in a peptide sequence stands for an amino acid residue, i.e., =N—CH(R)—CO— when it is at the N-terminus or —NH—CH(R)—CO— when it is not at the N-terminus, where R denotes the side chain of that amino acid residue. Thus, R is —CH($CH_3$)$_2$ for Val. Also, when the amino acid residue is optically active, it is the L-form configuration that is intended unless D-form is expressly designated. Note that the two Cys residues (i.e., $A^2$ and $A^7$) in formula (I) are linked together via a disulfide bond. However, for convenience a line which is used conventionally to denote a disulfide bond between two Cys residues is omitted herein. COE refers to —(C=O)—E and COOE refers to — (C=O)—O—E.

Administration of a pharmaceutically acceptable salt of an octapeptide covered by formula (I) into a patient whose disorder arises from biochemical activity mediated by NMB is also within the present invention. In other words, the octapeptides can be provided in the form of pharmaceutically acceptable salts such as acid addition salts, or metal complexes such as with zinc or iron. Examples of acid addition salts are (i) those made with organic acids such as acetic, lactic, pamoic, maleic, citric, malic, ascorbic, succinic, benzoic, palmitic, suberic, salicylic, tartric, methanesulfonic or toluenesulfonic acid; (ii) those made with polymeric acids such as tannic acid or carboxyethyl cellulose; and (iii) those made with inorganic acids such as hydrochloric acid, hydrobromic acid, sulfuric acid or phosphoric acid.

Other features and advantages of the present invention will be apparent from the following description of the preferred embodiments, and also from the appending claims.

BRIEF DESCRIPTION OF THE DRAWINGS

We first briefly describe the drawings.

DESCRIPTION OF THE PREFERRED EMBODIMENTS

Figure 1:
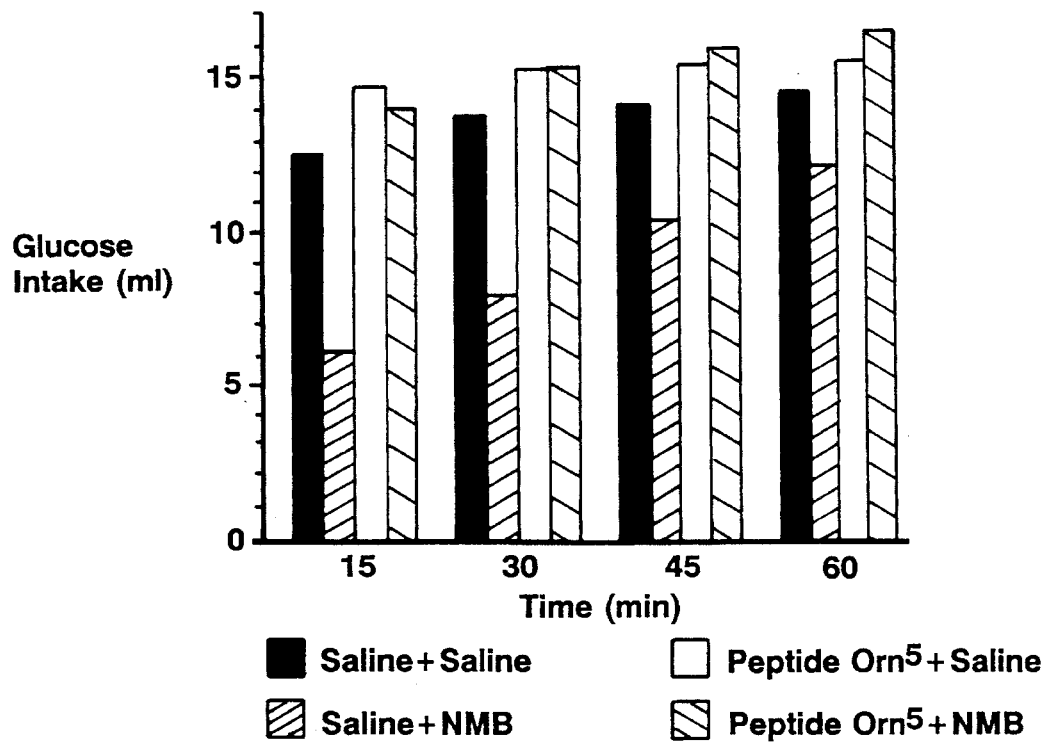
FIG. 1 is a graph showing the suppression of NMB stimulated food intake by an analog of the invention.

Octapeptides of the invention are synthesized on methylbenzhydrylamine resin using standard solid phase procedures and cleaved with hydrogen fluoride/anisol mixtures. The peptides are cyclized in dilute 90% acetic acid solution by titration with $I_2$ and purified by gel filtration on SEPHADEX™ G-25 (Aldrich, Milwaukee, Wis.) in 50% acetic acid and gradient elution on C18 silica using acetonitrile/0.1% trifluoroacetic acid buffers. See, e.g., Sasaki, Y. et al. *J. Med. Chem.*, 30:1162 (1987); Stewart, J. M. et al. Solid Phase Peptide Synthesis, 2nd Ed., Pierce Chemical Co., Rockford, Ill. (1984); and Coy, D. H. et al. *Tetrahedron*, 44:835 (1988). Homogeneity is assessed by thin layer chromatography ("TLC"), analytical HPLC, amino acid analysis and mass spectrometry. Preferably, homogeneity should be determined to be >96% for each peptide. Example 1 below is a detailed description regarding the synthesis of peptide Dab$^5$. Other peptides of the invention can be prepared by making appropriate modifications, within the ability of someone of ordinary skill in the art, of the synthetic methods disclosed herein.

The NMB analogs of the invention are screened in binding assays to determine their respective affinities for the NMB, GRP, and somatostatin receptors. See Examples 2, 3 and 4, respectively. Agonists of the NMB receptor have been shown to stimulate the generation of inositol phosphates. Wang, et al, *J. Biochem.*, 286:641–648 (1992). In Example 5 below, an inositol phosphate turnover assay measured the ability of the NMB analogs to antagonize the NMB receptor activation. In Example 6 below, an in vivo assay demonstrated the ability of the NMB analogs of the invention to block suppression of food intake produced by NMB.

The NMB analogs of this invention behave as potent antagonists of the NMB receptor. NMB has been shown to stimulate the growth of cancer cell lines (Moody, et al. *J. Pharmacol.*, 263:1 (1992); Wang, et al., *Biochem. J.*, 286:641 (1992)). As NMB antagonists the analogs of this invention can be used to treat cancers such as small cell lung tumors and glioblastomas. In addition, NMB has been shown to suppress food intake (Kirkman, et al., Society for the Study of Ingestive Behavior, Toronto, Canada). The analogs of the invention can be used to stimulate food intake to treat eating disorders such as anorexia or those resulting from cancer or AIDS. Furthermore, NMB has also been shown to decrease gastrin release, Kawai, et al., *Endocrinol. Japan*, 37(6):857 (1990). The analogs of the invention, thus, can be used to stimulate gastrin release in patients who are producing insufficient amounts of gastrin.

The analogs of the invention are also highly selective for the NMB receptor. The analogs of the invention will, therefore, have reduced cross-reactivity with both of these receptors. For example, other agonists of the somatostatin receptors may inhibit growth hormone release or disturb carbohydrate metabolism by the agonists' inhibition of insulin release.

The dose of the compound of the present invention for treating the above-mentioned diseases varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as a "therapeutically effective amount".

The formulations are presented in unit dosage form and are prepared by any of the methods well known in the art of pharmacy. All methods include the step of bringing the active ingredient(s) into association with the carrier which constitutes one or more accessory ingredients. In general, the formulations for tablets or powders are prepared by uniformly and intimately blending the active ingredient with finely divided solid carriers, and then, if necessary as in the case of tablets, forming the product into the desired shape and size.

Without further elaboration, it is believed that one skilled in the art can, based on the description herein, utilize the present invention to its fullest extent. The following specific embodiments are, therefore, to be construed merely as illustrative, and not limitative of the remainder of the disclosure in any way. All publications cited herein are incorporated by reference.

EXAMPLE 1

Synthesis of Boc-D-Nal-S-methylbenzyl-Cys-O-bromobenzyl-oxycarbonyl-Tyr-D-Trp-N-benzyloxycarbonyl-Dab-Val-S-methylbenzyl-Cys-Nal-benzhydrylamine resin was as follows. Benzhydrylamine-polystyrene resin (Advanced Chem Tech, Inc., Louisville, Ky.) (0.7 g, 0.3 mmole) in the chloride ion form was placed in the reaction vessel of an Advanced Chem Tech™ peptide synthesizer programmed to perform the following reaction cycle: (a) methylene chloride; (b) 33% trifluoroacetic acid in methylene chloride (2 time for 1 and 25 min each); (c) methylene chloride; (d) ethanol; (e) methylene chloride; (f) 10% triethylamine in chloroform.

The neutralized resin was stirred with t-butyloxy-carbonyl("Boc")-Nal and diisopropylcarbodiimide (1.5 mmole each) in methylene chloride for 1 hr and the resulting amino acid resin was then cycled through steps (a) to (f) in the above wash program. The following amino acids (0.9 mmole) were then coupled successively by the same procedure: Boc-S-methylbenzyl-Cys, Val, Boc-N-benzyloxycarbonyl-Dab, Boc-D-Trp, Boc-O-bromobenzyloxycarbonyl-Tyr, and Boc-S-methyl-benzyl-Cys and Boc-D-Nal. After washing and drying, the completed resin weighed 1.13 g.

Using the completed resin, H-D-Nal-Cys-Tyr-D-Trp-Lys-Dab-Cys-Nal-NH$_2$ was prepared. The peptide resin obtained above (1.13 g, 0.5 mmole) was mixed with anisole (5 ml), dithiothreitol (100 mg) and anhydrous hydrogen fluoride (35 ml) at 0° C. and stirred for 45 min. Excess hydrogen fluoride was evaporated rapidly under a stream of dry nitrogen. Free peptide was precipitated and washed with ether. The crude peptide was then dissolved in 250 ml of 90% acetic acid to which was added a concentrated solution of $I_2$/MeOH until a permanent brown color was observed. Excess $I_2$ was removed by addition of ascorbic acid and the solution was reduced to a small volume by evaporation. The crude peptide solution was applied to a column (2.5×90 cm) of SEPHADEX™ G-25 and eluted with 50% acetic acid. Fractions containing a major component by UV absorption and TLC were then pooled, reduced to a small volume by evaporation and applied to a column (1.5×70 cm) of VYDAC® octadecylsilane silica (10–15μ) (Vydac, Hesperia, Calif.) followed by elution with a linear gradient of acetonitrile in 0.1% trifluoroacetic acid in water. Fractions were examined by TLC and analytical high performance liquid chromatography and pooled to give maximum purity.

Repeated lyophilization of the solution from water gave 97 mg of the product as a white, fluffy powder. The product was found to be homogeneous by HPLC and TLC. Amino acid analysis of an acid hydrolysate and FAB MS confirmed the composition of the octapeptide.

EXAMPLE 2

NMB Receptor Binding Assay

The procedure for transfecting the rat NMB receptor into BALB-3T3 fibroblasts is discussed in Wada, et al., *Neuron*, 6:4221-430 (1991) and Benya, et al., *Mol. Pharmacol.*, 42:1058 (1992). Membranes for the NMB receptor binding assay were obtained by homogenizing BALB-3T3 fibroblasts, transfected with the rat NMB receptor, with a POLYTRON™ tissue homogenizer (setting 6, 15 sec) (Brinkman, Westbury, N.Y.) in ice-cold 50 mM Tris-HCl (Buffer A) (Sigma Chemicals, St. Louis, Mo.) and centrifuging twice at 39,000×g (10 min), with an intermediate resuspension in fresh Buffer A. The final pellets were resuspended in the 50 mM Tris-HCl, containing 0.1 mg/ml bacitracin (Sigma Chemicals, St. Louis, Mo.), and 0.1% bovine serum albumin (BSA) (Buffer B) (Sigma Chemicals, St. Louis, Mo.), and held on ice for the receptor binding assay. Aliquots (0.4 ml) were incubated with 0.05 ml of [$^{125}$I-Tyr$^4$] bombesin (~2200 Ci/mmole) (New England Nuclear, Boston, Mass.) in Buffer B, with and without 0.05 ml of unlabeled NMB analogs. After a 30 min incubation (4° C.), the bound [$^{125}$I-Tyr$^4$] bombesin was separated from the free by rapid filtration through WHATMAN™ GF/B filters which had been previously soaked in 0.3% polyethyleneimine using a Brandel filtration manifold (Brandel, Gaithersberg, Md.). The filters were then washed three times with 5 ml aliquots of ice-cold Buffer A. Specific binding was defined as the total [$^{125}$I] bombesin bound minus that bound in the presence of 1 μM unlabeled NMB. Analogs of the invention had a high binding affinity for the NMB receptor. Examples of the NMB receptor binding assay results for three analogs of the invention were ($K_i$ values in nM) 47.4±10.3 (peptide Arg$^5$), 85.1±2.7 (peptide Dab$^5$), and 69.9±7.1 (peptide Orn$^5$).

EXAMPLE 3

GRP Receptor Binding Assay

Membranes for the GRP receptor binding assay were obtained by homogenizing cultured AR42J cells with a Polytron™ tissue homogenizer (setting 6, 15 sec) in ice-cold 50 mM Tris-HCl (Buffer A) and centrifuging twice at 39,000×g (10 min), with an intermediate resuspension in fresh Buffer A. The final pellets were resuspended in the 50 mM Tris-HCl containing 0.1 mg/ml bacitracin and 0.1% bovine serum albumin (BSA) (Buffer B) and held on ice for the GRP receptor binding assay. Aliquots (0.4 ml) were incubated with 0.05 ml of [$^{125}$I-Tyr$^4$] bombesin (~2200 Ci/mmole) in Buffer B, with and without 0.05 ml of unlabeled NMB analogs. After a 30 min incubation (4° C.), the bound [$^{125}$I]-Tyr$^4$] bombesin was separated from the free by rapid filtration through WHATMAN™ GF/B filters which had been previously soaked in 0.3% polyethyleneimine using a Brandel™ filtration manifold. The filters were then washed three times with 5 ml aliquots of ice-cold Buffer A. Specific binding was defined as the total [$^{125}$I-Tyr$^4$] bombesin bound minus that bound in the presence of 1 μM unlabeled GRP. Analogs of the invention had a weak binding affinity for the GRP receptor. Examples of the GRP receptor binding assay results for analogs of the invention were ($K_i$ values in nM) 2921±250 (peptide Arg$^5$) and 2632±216 (peptide Dab$^5$). Orn had a particularly weak affinity with a $K_i$ value >10,000.

EXAMPLE 4

Somatostatin Receptor Binding Assay

Membranes for the somatostatin receptor binding assay were obtained by homogenizing cultured AR42J acinar pancreas cells with a Polytron™ tissue homogenizer (setting 6, 15 sec), in ice-cold 50 mM Tris-HCl (Buffer A) and centrifuging twice at 39,000×g (10 min), with an intermediate resuspension in fresh Buffer A. The final pellets were resuspended in 10 mM Tris-HCl for the receptor binding assay. For determination of the $K_i$ values, the various concentrations of NMB analogs were incubated for 90 min at 25° C. with approximately 0.05 nM [$^{125}$I]MK-678 (University of Arizona, School of Medicine, Tucson, Ariz.) in 50 mM HEPES (pH 7.4)(Sigma Chemicals, St. Louis, Mo.) containing BSA (fraction V)(10 mg/ml) (Sigma Chemicals, St. Louis, Mo.), $MgCl_2$ (5 mM)(Sigma Chemicals, St. Louis, Mo.), aprotinin (200 KIU/ml)(Sigma Chemicals, St. Louis, Mo.) bacitracin (0.02 mg/ml), and phenylmethylsulphonyl fluoride (0.02 mg/ml)(Sigma Chemicals, St. Louis, Mo.). The final assay volume was 0.3 ml. The incubations were terminated by rapid filtration through GF/C filters (presoaked in 0.3% polyethylenimine) using a BRANDEL™ filtration manifold. Each tube and filter were then washed three times with 5 ml aliquots of ice-cold buffer. Specific binding was defined as the total [$^{125}$I]MK-678 bound minus that bound in the presence of 200 nM MK-678. A known cyclic octapeptide D-Nal-Cys-Tyr-D-Trp-Lys-Val-Cys-Nal-NH$_2$ (Lys$^5$) was disclosed in Orbuch et al., *Mol. Pharmacol.* 44:841 (1993), and had an extremely high affinity for the somatostatin receptor ($K_i$=0.84±0.53). In contrast, analogs of the invention had a much lower affinity, in a range of about one hundredth or one thousandth the $K_i$ value of Lys$^5$. For example, $K_i$ values (nM) for analogs of the invention were 54.2±9.6 (peptide Orn$^5$), 407±82 (peptide Dab$^5$) and, notably, 1032±113 (peptide Arg$^5$).

EXAMPLE 5

Inositol Phosphate Turnover Assay

For the measurement of inositol phosphate turnover, BALB-3T3 fibroblasts, transfected with the rat NMB receptor were harvested and resuspended in a phosphate-buffered saline solution containing 25 mM glucose (Sigma Chemicals, St. Louis, Mo.) and 75 mM sucrose (PBS+GS) and pre-incubated with 25 μCi/ml myo-[$^3$H] inositol (New England Nuclear, Boston, Mass.) for 60 min at 37° C. The cells were washed, resuspended in PBS+GS, and incubated with LiCl (100 mM) (Sigma Chemicals, St. Louis, Mo.) and the NMB analogs in a final volume of 0.30 ml. The reaction was terminated by the addition of chloroform/methanol (1:2)(Burdick & Johnson, Muskegeon, Mich.; Mallinckrodt, Paris, Ky.), and the total [$^3$H] inositol phosphates were isolated as described in Snider et al., *J. Neurochem.*, 47:1214 (1986). Peptide Dab$^5$ is a potent agonist of the NMB receptor, with a $K_i$ (μM) of 78.1±25.9 in the inositol phosphate turnover assay.

EXAMPLE 6

In vivo Suppression of Food Intake

Individually housed male Sprague-Dawley rats (Charles River, n=8) weighing 450–500 g. were maintained in a temperature-controlled room on a 12:12 hr. light: dark cycle. Rats were adapted to a 5 hr. food deprivation schedule followed by 60 min. access to a 0.5 kcal/ml glucose solution. Rats were injected intraperitoneally with either 0.9% saline (1.0 ml/kg) or 100 nmole/kg of peptide Orn$^5$. One minute later, rats were injected intraperitoneally with either saline, 32.0 nmole/kg NMB, or 3.2 nmole/kg NMC (GRP18-27), the biologically active portion of GRP. These agonist doses have previously been determined to reliably suppress intake in this experimental paradigm, Ladenheim, et al., *Amer. Physiol. Soc.* R263-R266 (1991). Five minutes after the second injection, the glucose solution was presented and intake was monitored at 15, 30, 45 and 60 min. Each rat received all four conditions for both NMB and NMC. Administration of either the agonists or antagonist was separated by at least 48 hr. Data were statistically analyzed using a 4 (injection)×4 (time) analysis of the variance followed by planned t-test comparisons for each agonist. Because intake following the baseline condition (Saline+Saline) for both sets of experiments was not significantly different (p>0.5) these were averaged and used to compare with effects of the agonists and peptide Orn$^5$.

Figure 2:
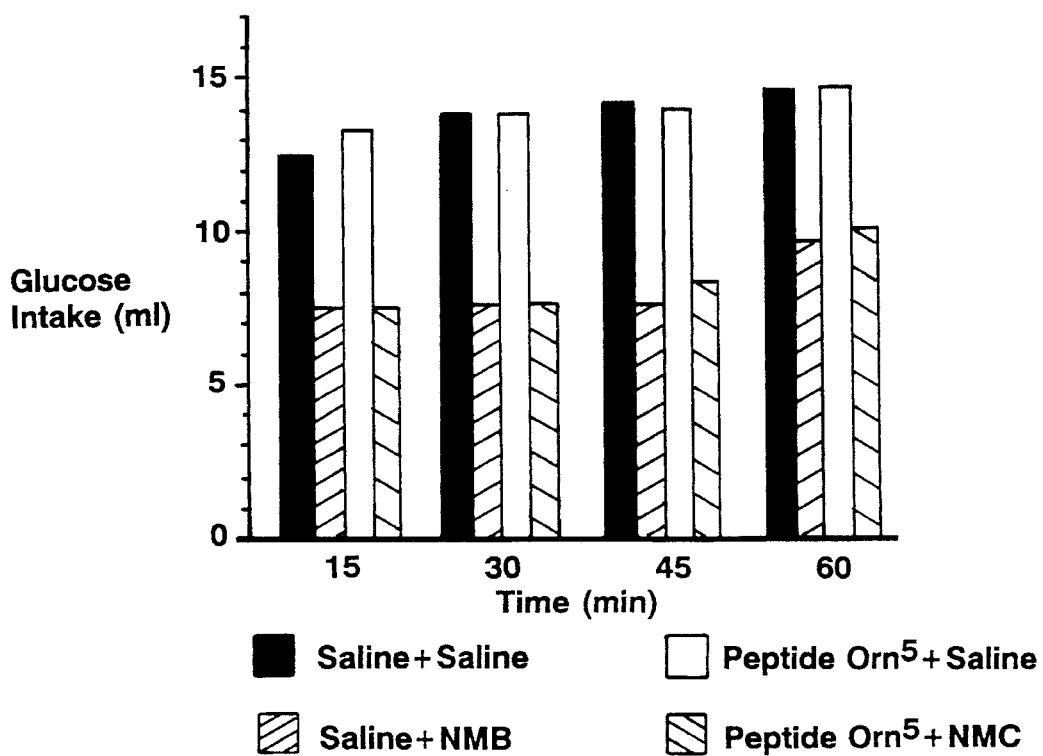
FIG. 2 is a graph showing suppression of NMC stimulated food intake by an analog of the invention.

The results showed that both NMB (FIG. 1) and NMC (FIG. 2) significantly suppressed food intake compared to baseline intake at all time points (p<0.01). Prior administration of 100 nmole/kg of peptide Orn$^5$ completely blocked the suppression of glucose intake produced by NMB. Intake for peptide Orn$^5$+NMB and peptide Orn$^5$+Saline conditions was greater than in the Saline+Saline condition (p<0.01). In contrast to NMB, prior administration of peptide Orn$^5$ had no effect on suppression of intake produced by NMC, in that suppression of intake in the Saline+NMC condition was not significantly different from intake in the peptide Orn$^5$+NMC condition (p>0.5).

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:
1. A cyclic octapeptide of the formula:

$$\begin{array}{c} R_1 \\ \phantom{R}\diagdown \\ \phantom{RR}A^1-Cys-A^3-D-Trp-A^5-A^6-Cys-A^8-R_3 \\ \phantom{R}\diagup \\ R_2 \end{array}$$

wherein:

$A^1$ is D-Nal or D-Trp;

$A^3$ is Phe, F$_5$-Phe, or X-Phe wherein X is a halogen, NO$_2$, CH$_3$, or OH;

$A^5$ is —NH—CH(Y)—CO— wherein Y is (CH$_2$)$_m$—R$_4$—N(R$_5$)(R$_6$) or (CH$_2$)$_n$—R$_4$—NH—C(R$_7$)—N(R$_5$)(R$_6$);

$A^6$ is the D— or L— isomer of an amino acid selected from the group consisting of Thr, Leu, Ile, Nle, Val, and Abu;

$A^8$ is Nal or Trp;

m is 1, 2, or 3;

n is 1, 2, 3, 4 or 5;

each of R$_1$ and R$_2$, independently, is H, E, COE, or COOE wherein E is C$_{1-12}$ alkyl, C$_{2-12}$ alkenyl, C$_{2-12}$ alkynyl, phenyl, naphthyl, C$_{7-12}$ phenylalkyl or alkylphenyl, C$_{8-12}$ phenylalkenyl or alkenylphenyl, C$_{8-12}$ phenylalkynyl or alkynylphenyl, C$_{11-20}$ naphthylalkyl or alkylnaphthyl, C$_{12-20}$ naphthylalkenyl or alkenylnaphthyl, or C$_{12-20}$ naphthylalkynyl or alkynylnaphthyl, provided that when one of R$_1$ or R$_2$ is COE or COOE, the other must be H;

R$_4$ is C$_6$H$_4$ or absent;

R$_7$ is =NR$_8$, =S, or =O; and each of R$_3$, R$_5$, R$_6$, and R$_8$, independently, is H or E.

2. A cyclic octapeptide of claim 1, wherein Y is (CH$_2$)$_m$—R$_4$—N(R$_5$)(R$_6$).

3. A cyclic octapeptide of claim 2, wherein R$_4$ is absent.

4. A cyclic octapeptide of claim 3, wherein m is 2 or 3, and each of R$_5$ and R$_6$ independently is H or C$_1$—C$_5$ alkyl.

5. A cyclic octapeptide of claim 4, wherein A$^3$ is Phe or para-substituted X-Phe where X is Cl, F, or OH.

6. A cyclic octapeptide of claim 5, wherein A$^1$ is D-Nal and A$^8$ is Nal.

7. A cyclic octapeptide of claim 6, wherein A$^3$ is Tyr and A$^6$ is Val.

8. A cyclic octapeptide of claim 4, wherein A$^5$ is Dab or Orn.

9. A cyclic octapeptide of claim 8, wherein A$^3$ is Phe or para-substituted X-Phe where X is Cl, F, or OH.

10. A cyclic octapeptide of claim 8, wherein A$^1$ is D-Nal and A$^8$ is Nal.

11. A cyclic octapeptide of claim 8, wherein A$^3$ is Tyr and A$^6$ is Val.

12. A cyclic octapeptide of claim 11, having the formula: H$_2$-D-Nal-Cys-Tyr-D-Trp-Dab-Val-Cys-Nal-NH$_2$.

13. A cyclic octapeptide of claim 11, having the formula: H$_2$-D-Nal-Cys-Tyr-D-Trp-Orn-Val-Cys-Nal-NH$_2$.

14. A cyclic octapeptide of claim 1, wherein Y is (CH$_2$)$_n$—R$_4$—NH—C (R$_7$)—N(R$_5$)(R$_6$).

15. A cyclic octapeptide of claim 14, wherein R$_4$ is absent, and R$_7$ is =NR$_8$.

16. A cyclic octapeptide of claim 15, wherein n is 2, 3, or 4; and each of R$_5$, R$_6$, and R$_8$, independently, is H or C$_1$–C$_5$ alkyl.

17. A cyclic octapeptide of claim 16, wherein A$^3$ is Phe, or para-substituted X-Phe where X is Cl, F, or OH.

18. A cyclic octapeptide of claim 17, wherein $A^1$ is D-Nal and $A^8$ is Nal.

19. A cyclic octapeptide of claim 18, wherein $A^3$ is Tyr and $A^6$ is Val.

20. A cyclic octapeptide of claim 16, wherein $A^5$ is Arg.

21. A cyclic octapeptide of claim 20, wherein $A^3$ is Phe, or para-substituted X-Phe where X is Cl, F, or OH.

22. A cyclic octapeptide of claim 21, wherein $A^1$ is D-Nal and $A^8$ is Nal.

23. A cyclic octapeptide of claim 21, wherein $A^3$ is Tyr and $A^6$ is Val.

24. A cyclic octapeptide of claim 23, wherein said octapeptide is of the formula:

$H_2$-D-Nal-Cys-Tyr-D-Trp-Arg-Val-Cys-Nal-$NH_2$.

* * * * *